United States Patent [19]
Frisbee et al.

[11] Patent Number: 6,086,920
[45] Date of Patent: Jul. 11, 2000

[54] DISINTEGRATABLE MICROSPHERES

[75] Inventors: Steven E. Frisbee, Reston, Va.; John Getz, Clearwater, Fla.; Joseph Cascone, Chantilly, Va.

[73] Assignee: Fuisz Technologies Ltd., Chantilly, Va.

[21] Appl. No.: 09/132,923

[22] Filed: Aug. 12, 1998

[51] Int. Cl.[7] ........................................ A61K 9/14
[52] U.S. Cl. ................ 424/489; 424/497; 424/490; 424/465; 424/468; 424/451
[58] Field of Search ..................... 424/489, 497, 424/490, 464, 465, 468, 451; 514/722.5

[56] References Cited

U.S. PATENT DOCUMENTS

| | | | |
|---|---|---|---|
| 5,458,823 | 10/1995 | Perkins et al. | 264/8 |
| 5,464,632 | 11/1995 | Cousin et al. | 424/465 |
| 5,593,685 | 1/1997 | Bye et al. | |

FOREIGN PATENT DOCUMENTS 0 636 364 A1  7/1994  European Pat. Off. .

*Primary Examiner*—Thurman K. Page
*Assistant Examiner*—Amy E Pulliam
*Attorney, Agent, or Firm*—Richard D. Schmidt

[57] ABSTRACT

Microspheres which disintegrate quickly in water are composed of bio-affecting agent(s), disintegrant(s) and spheronization aid(s). The microspheres, which may have taste-masking coatings, are useful in making comestible units, such as pharmaceutical dosage forms.

14 Claims, 2 Drawing Sheets

DISINTEGRATABLE MICROSPHERES

FIELD OF THE INVENTION

The invention deals with novel particles used to formulate fast dissolving pharmaceutical dosage forms. The particles have adequate integrity when dry, ie., when being formulated and processed into comestible units, but quickly lose their integrity and disintegrate when dosage forms containing them are in an aqueous environment, such as that found in the mouth or the gastrointestinal tract.

BACKGROUND OF THE INVENTION

The particles contain, as essential constituents, drugs or other bio-affecting substances, disintegrants and spheronization aids. They are useful in a variety of comestible units, particularly in pharmaceutical dosage forms having optional tastemasking coatings.

The use of disintegrants in solid drug dosage forms is discussed in the following disclosures:

U.S. Pat. No. 5,464,632 recites, at column 1, lines 47+, the use of "disintegrating agents of the carboxymethylcellulose type or insoluble reticulated PVP type." Such agents are mixed with polymer-coated dry particles or with sugar spheres that have been coated with drug and polymer. The disintegrating agent is not contained in a drug-containing core.

European Patent Office Publication No. 0636364A1 (from Application No. 94305533.5), published Jul. 25, 1994, teaches compressed wafers made from coated drug particles. The coated particles contain a drug substrate coated with a blend of polymers. The coated particles are blended with a water-disintegratable carbohydrate and a binder. The disintegrant used (i.e., a carbohydrate) is not contained in the drug-containing core.

SUMMARY OF THE INVENTION

The invention relates to novel particles, comestible units containing them, and processes for making each of these.

The particles are preferably microspheres which give 100% aqueous dissolution of bio-affecting agents therein, in 30 minutes or less. The particles are thermoformed from compositions containing bio-affecting agent(s), disintegrants, and spheronization aid(s). Lubricant(s) may also be included.

One would expect that, during thermoforming, the disintegrant would become coated, or encapsulated, with one or more of the other ingredients in the microspheres. Surprisingly, no such coating takes place. The microspheres made herein are water sensitive, so that, when hydrated, water readily interacts with their surfaces, resulting in rapid rupture into fragments, from which the bio-affecting agents therein are dissolved quickly.

In dissolution tests on disclosed embodiments, drug-containing masses made using compositions of the invention readily fragmented in water to yield smaller particles which enhanced dissolution of the bio-affecting agent(s) therein, i.e., complete solution in 30 minutes or less. The faster dissolution of the agent(s) in these microspheres should lead to more rapid absorption.

THE DRAWINGS

The drawing figures illustrate the improved dissolution properties of the microspheres of the invention.

DETAILED DESCRIPTION OF THE INVENTION

Figure 1:
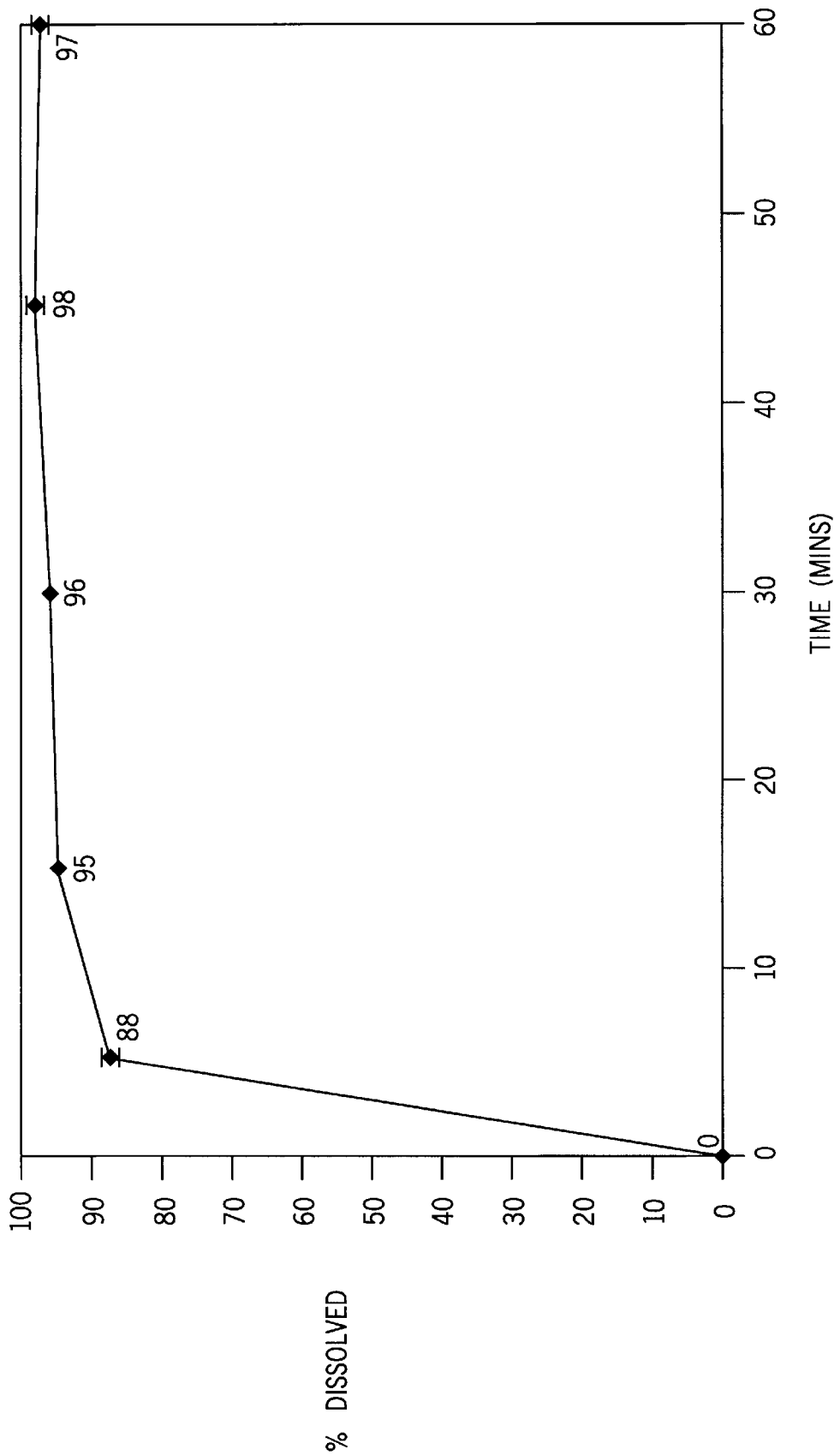
FIG. 1 is a graph showing the dissolution properties obtained with spheres of the invention.
Figure 2:
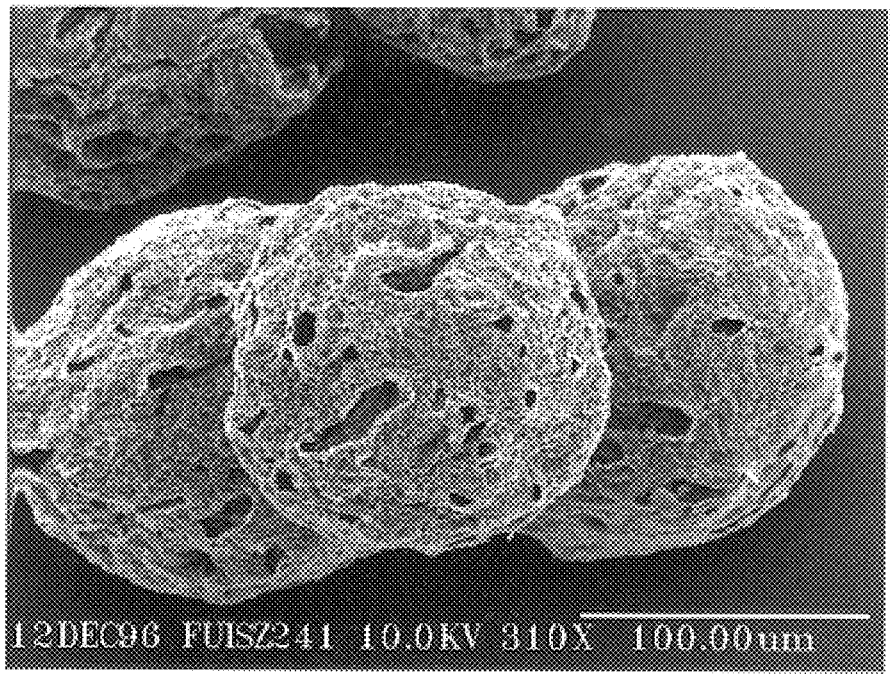
FIGS. 2 and 3 show photomicrographs of hydrated spheres, with FIG. 2 being conventional spheres and FIG. 3 being spheres made using the invention.
Figure 3:
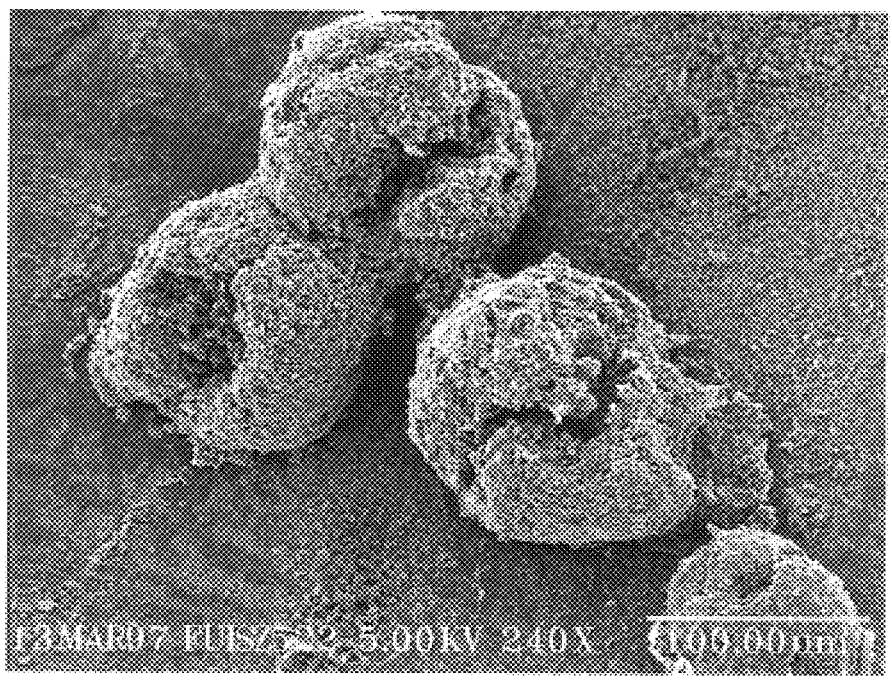

Unless otherwise indicated, all percentages herein are weight percents, based on total composition weight. All disclosures referred to are incorporated herein by reference.

Applicants have found that certain water-insoluble disintegrants will, when used in certain quantities and in conjunction with bio-affecting agent(s) and spheronization aid (s), produce spherical masses in which they act as moisture-sensitive ingredients for the masses and for larger aggregates containing them, i.e., tablet or capsule dosage forms.

Throughout the description "masses," "microspheres" and "particles" refer to the generally spherical masses made in accordance herewith.

By "moisture-sensitive ingredients," Applicants mean ingredients which, upon hydration or other contact with moisture: (1) produce a honeycomb-like structure in masses directly thermoformed therefrom and (2) cause the masses into which they are incorporated to rupture or disintegrate into fragments.

Applicant uses "bio-affecting agents" and "active agents" throughout to mean drugs and other substances which exert a biological effect in a host, preferably a human being or other mammalian host, after administration.

Unlike simple active/solubilizer combinations, Applicants' system is not binary. Instead, it is a three-component system that requires the use of active agent, disintegrant, and spheronization aid components. Each component may contain multiple ingredients.

It is preferred that the active agents used be such that they supply some hydrophilicity to the compositions. Applicants believe that the hydrophilicity of the active agent in the three-component system causes the normally hydrophobic disintegrant and spheronization aid components to become disintegratable. Optionally, hydrophilic materials may be added to enhance the solubility of the active agent(s).

Stated in engineering terms, the thermoformed particles contain ingredients that are usually conventionally processed dry (e.g., disintegrants and optionally hydrophilic drugs) or wet (e.g., spheronization aids). By combining them via a thermoforming process which is neither wet nor dry, e.g., using "liquiflash conditions", Applicants do not destroy their original hydrophilic or hydrophobic character. As a result, when the particles of the invention are hydrated in the mouth or the gastrointestinal tract, the hydrophilic and hydrophobic material(s) therein still respond to the presence of moisture.

In some embodiments, microspheres are made using disintegrants along with drug(s), spheronization aids and permeation enhancer(s). The optional permeation enhancers, e.g., sucrose and the like, serve to improve the fragmentation of the microspheres. Concentration levels of permeation enhancers will range from 0 to 25%.

In other embodiments, the drug/disintegrant/spheronization aid combination is enhanced further by the addition of one or more hydrophilic material(s), such as surfactant(s). These hydrophilic agents are optionally used to provide pathways for hydration of the thermoformed particles. However, hydrophilic agents are generally not needed when the concentration of disintegrant(s) is 20% or more. Amounts of hydrophilic agents range from about 0 to about 30%, with amounts of about 5% to about 15% being typical.

The advantages of the invention include:

Ease of production. Microspheres can be made using the invention in the absence of special solvents, prolonged heating or special safety precautions.

Ease of handling. Due to their shape and size, Applicants' microspheres are easy to pour, transport, coat, and blend with other ingredients, e.g., tableting excipients, fondants, etc. The storage limitations of the incipient(s) and optional penetration enhancers are the only special handling considerations.

Other advantages will be apparent after considering Applicants' description and claims.

I. The Particles

A. Composition and Shape

The compositions used to make the particles contain three essential components in the weight percentage ranges set out in the following table:

|  | Broad % | Preferred % | Most Preferred % |
| --- | --- | --- | --- |
| Bio-affecting Agent | 50–90 | 65–75 | 68 |
| Disintegrant | 2–40 | 10–20 | 6 |
| Spheronization Aid | 5–15 | 10–20 | 16 |

These components are combined along with other ingredients, such as excipients under conditions described herein, to yield particles.

Optional excipients include at least one material selected from the group consisting of colorants, perfumes, lubricants, fillers, and flavor enhancers. When used, they are present at levels of about 0.5 to about 20%.

When coated for taste-masking or other purposes, the particles have on their surfaces about 10% to about 40% of one or more suitable coatings.

The bio-affecting agents useful in the invention include a wide variety of active ingredients, including combinations thereof.

The active ingredients useful herein can be selected from a large group of therapeutic agents. Respective classes include those in the following therapeutic categories: ace-inhibitors; alkaloids; anabolic agents; anabolic drugs; analgesics; antacids; anti-allergy agents; anti-anginal drugs; anti-arrhythmia agents; antiasthmatics; antibiotics; anticholesterolemics; anticoagulants; anticonvulsants; antidepressants; antidiabetic agents; antidiarrheal preparations; antiemetics; antihistamines; antihypertensives; anti-infectives; anti-inflammatories; antilipid agents; antimanics; antimigraine agents; antinauseants; antiobesity agents; antiparasitics; antipsychotics; antipyretics; antispasmodics; antistroke agents; antithrombotics; antithyroid preparations; antitumor agents; antitussives; antiulcer agents; antiuricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diclofenac, diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents which may be used in the invention include: acetaminophen; acetic acid; acetylsalicylic acid, including its buffered forms; acrivastine; albuterol and its sulfate; alcohol; alkaline phosphatase; allantoin; aloe; alprozolam; aluminum acetate, carbonate, chlorohydrate and hydroxide; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium; calcium carbonate; camphor; captopril; cascara sagrada; casinate and hydroxide; castor oil; cefaclor; cefadroxil; cephalexin; cetrizine and its hydrochloride; cetyl alcohol; cetylpyridinium chloride; chelated minerals; chloramphenicol; chlorcyclizine hydrochloride; chlorhexidine gluconate; chloropentostatin; chloroxylenol; chlorpheniramine and its maleates and tannates; chlorpromazine; cholestyramine resin; choline bitartrate; chondrogenic stimulating protein; cimetidine and its hydrochloride; cinnamedrine hydrochloride; ciprofloxacin HCl; citalopram; citric acid; clarithromycin; clemastine and its fumarate; clonidine and its hydrochloride salt; clorfibrate; cocoa butter; cod liver oil; codeine and its fumarate and phosphate; cortisone acetate; cyanocobalamin; cyclizine hydrochloride; cyproheptadine and its hydrochloride; danthron; dexbromopheniramine maleate; dextromethorphan and its hydrohalides; diazepam; dibucaine; dicholoralphenazone; diclofenac and its alkali metal salts; digoxin; dihydroergotamine and its hydrogenates/mesylates; diltiazem; dimethicone; dioxybenzone; diphenhydramine, its citrate and its hydrochloride; divalproex and its alkali metal salts; docusate calcium, potassium, and sodium; doxycycline hydrate; doxylamine succinate; dronabinol; efaroxan; elitripton; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; 5-fluorouracil (5-FU); fluoxetine and its hydrochloride; folic acid; fosphenytoin; furosemide; gabapentan; gemfibrozil; gentamicin; glipizide; glycerine; glyceryl stearate; granisetron and its hydrochloride; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isometheptene mucate; isosorbide and its mono- and dinitrates; isoxicam; itraconazole; kaolin; ketamine; ketoprofen; lactic acid; lanolin; lecithin; leuprolide acetate; lidocaine and its hydrochloride salt; lifinopril; liotrix; loratadine; lovastatin; luteinizing hormore; luteinizing hormone replacement hormone (LHRH); magnesium carbonate, hydroxide, salicylate, and trisilicate; meclizine and its hydrochloride; meclofenamic acid and its sodium salt; medroxyprogesterone acetate; mefenamic acid; menthol; meperidine hydrochloride; metaproterenol sulfate; metformin; methenamine mandelate; methscopolamine and its nitrates; methsergide and its maleate; methyl cellulose;

methyl nicotinate; methyl salicylate; methsuximide; metoclopramide and its halides/hydrates; metoprotol tartrate; metronidazole and its hydrochloride; miconazole nitrate; mineral oil; minoxidil; morphine; naproxen and its alkali metal salts; neomycin sulfate; niacin; niacinamide; nicotinamide; nicotine; nifedipine; nimesulide; nitroglycerine; nonoxynol-9; norethindrone and its acetate; nystatin; octoxynol-9; octyl dimethyl PABA; octyl methoxycinnamate; omega-3 polyunsaturated fatty acids; omeprazole; ondansetron and its hydrochloride; oxolinic acid; oxtriphylline; oxybenzone; padimate-O; para-aminobenzoic acid (PABA); paramethadione; pentaerythritol tetranitrate; pentastatin; pentobarbital sodium; peppermint oil; perphenazine; pheneizine sulfate; phenindamine and its tartrate; pheniramine maleate; phenobarbital; phenol; phenolphthalein; phenylephrine and its tannates and hydrochlorides; phenylpropanolamine and its hydrochloride salt; phenytoin; pirnenol; piroxicam and its salts; polymicin B sulfate; potassium chloride and nitrate; pramiracetin; pramoxine and its hydrochloride salt; prazepam; procainamide hydrochloride; procaterol; prochlorperazine and its maleate; promethazine and its hydrochloride; propanolol and its hydrohalides; propoxyphene and its hydrochloride and napsylate; pseudoephedrine and its sulfates and hydrochlorides; pyridoxine; pyrilamine and its hydrochlorides and tannates; quinapril; quinestrol; quinidine gluconate and sulfate; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; terfenadine; tetracycline hydrochloride; theophylline; thiethylperazine and its maleate; thioperidone; timolol and its maleate; tolmetin; tolnaftate; tretinoin; triazolam; triclosan; trimethobenzamide and its hydrochloride; trimetrexate; tripelennamine and its hydrochloride; tripolidine hydrochloride; undecylenic acid; vancomycin; verapamil Hcl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

Particularly useful active agents are water-insoluble solid agents whose dissolution and release properties are enhanced by including them in applicants' microspheres and using the spheres in the presence of water or other hydrating material(s). Suitable agents include antacids, $H_2$ antagonists, analgesics, including nonsteroidal anti-inflammatory drugs (NSAIDs), and anticholesterolemics.

Antacid dosages can be prepared using the ingredients calcium carbonate alone or in combination with magnesium hydroxide and/or aluminum hydroxide. Moreover, antacids can be used in combination with $H_2$-antagonists.

$H_2$-antagonists which are contemplated for use in the present invention include cimetidine, ranidine hydrochloride, famotidine, nizatidine, ebrotidine, mifentidine, roxatidine, pisatidine and aceroxatidine.

Analgesics include aspirin, acetaminophen, acetaminophen plus caffeine, and nonsteroidal anti-inflammatory drugs (NSAIDS), e.g., aspirin, ibuprofen and nimesulide.

Anticholesterolemics include a wide variety of lipid lowering agents. Among them are bile acid sequestrants, HMG-CoA reductose inhibitors, and statins, e.g., lovastatin, provastatin and the like.

Among the preferred drugs to be used herein are: aspirin, ibuprofen, flurbiprofen, and nimesulide. Ibuprofen is preferred.

Other embodiments employ nontoxic N-methyl-D-aspartate (NMDA) receptor antagonists and analgesics. The active agents can be together in one particle or in separate particles, with microspheres being preferred particles.

Disintegrants useful herein include a wide variety of substances. Among them are cross-linked polyvinylpyrrolidone (also called "Povidone," "Kollidon" and "Polyplasdone"); croscarmellose sodium (also called "Ac-Di-Sol," "modified cellulose gum," and "cross-linked carboxymethyl cellulose sodium"). Mixtures are operable. Cross-linked polyvinylpyrrolidone is very effective.

Typically, disintegrants are used in formulations for comestible units at concentration levels of 0.5% to 5% as excipients. In the invention, one or more of these agents is used at elevated levels, ie., levels of about 5% to about 25%, based on total composition weight.

The concentration of disintegrant used in Applicants' formulations depends upon the hydrophilicity of the active agent(s) present. For ibuprofen, concentrations of about 10% to about 20% are useful.

The third key ingredient is the spheronization aid component. Useful aids include glyceryl behenate (also called "Compritol 888 ATO"), glyceryl monostearate (sold as "Myvaplex 600P") and the like. Mixtures can be used.

An optional, but preferred, fourth ingredient is a hydrophilic component. Suitable hydrophilic agents include polyethylene glycol (32) glyceryl esters ("Gelucires"), sugars, salts, (e.g., sodium chloride), surface active agents (e.g., "Pluronics"), sodium lauryl sulfate, and the like. Mixtures can be used.

Other ingredients which may be included in the compositions to be thermoformed are categorized as lubricants, permeation enhancers, fillers, flavor enhancers, stabilizers and the like.

Suitable fillers are talc, silica and the like.

Useful flavor enhancers are natural and artificial flavors and sweeteners.

Mixtures of one or several substances from each of these categories of ingredients can be used.

Generally, the ingredients other than components (a), (b), and (c) will constitute only from 0% to about 5% of the overall products' weight. In capsules or tablets, the particles are present at levels of about 10% to about 60%, with the remainder being one or more coatings/other ingredients which enhance consumer acceptability, e.g., taste-masking coatings.

The particles made using the invention are generally round or spherical and are preferably microspheres of about 150 to about 200 microns diameter. However, similarly sized particles of non-spherical, e.g., elliptical, shape are useful.

B. Procedures

The particles of the invention are typically microspheres made using suitable thermoprocessing or thermoforming conditions. In general, thermoforming techniques which employ processing parameters similar to those described here may be used.

The microspheres can be made using spinning devices and processes described in U.S. Pat. No. 5,458,823 and U.S. application Ser. No. 08/874,515, now abandoned filed Jun. 13, 1997.

These descriptions, and others described in patents and applications owned by applicants' assignee, relate to the use of "liquiflash conditions" to produce discrete particles having different morphologies from those of the starting materials from which they are produced.

"Liquiflash conditions" are generally those under which the starting material(s), called a feedstock, is rapidly heated just to the point at which it undergoes intraparticulate flow and partially deforms or liquefies so that it can pass through openings in a suitable spinning device. The passage of the liquiflash particles through openings is in response to the centrifugal forces within the spinning head, which forces "expel" the particles, as discrete solids, out of the device and into the atmosphere. The expelled materials instantly reform into particles, without the application of external shaping forces, which have different morphologies, i.e., internal crystalline character, from those of the feedstocks.

Because heat-sensitive bio-affecting agents are sometimes used, it is often desirable to use such devices which ensure that the amount of time that the agent(s) are exposed to heat is kept to a minimum. Also, it is preferred that the materials not be heated beyond the point at which they reach liquiflash conditions.

Applicants have found that one particular spinning device is highly useful in making the microspheres of the invention. In U.S. Pat. No. 5,458,823, a spinning device is described which uses a spinning head including a base and a cover. A plurality of closely spaced heating elements are positioned between the base and cover, forming a barrier through which the material to be processed passes. In use, the head rotates and the heating elements are heated to temperatures which bring about liquiflash conditions in the materials being processed. As the spinning head rotates, the centrifugal force created by its rotation expels the material through spaces between the heating elements. The material forms discrete, generally spherical particles as it exits.

The production of microspheres for use in the subject invention may be optimized by the use of a V-groove insert inside the spinner head. The insert is described in pending U.S. patent application Ser. No. 08/874,515, now abandoned, filed Jun. 13, 1997. The insert has grooves therein, which grooves have a uniform depth and width through their length, so that highly uniform discrete microspheres or other particles are produced. Using this or a similar insert, the spinning device is operated at 50 to 75 Hz, at about 10 to 25% power, and at temperatures which yield liquiflash conditions.

It should be noted that "liquiflash conditions" vary with the properties of the material, or feedstock, being processed. Since the feedstocks contain many substances in varying amounts, the parameters need to yield "liquiflash conditions" for a particular mixture must be ascertained by processing small quantities or samples before processing large ones.

One feature of the subject particles is the "honeycomb" structure which results when they are first hydrated, i.e., shortly after contact with moisture. This structure and the subsequent "rupture" of the particles into multiple fragments in the presence of water or other hydrating fluid are properties of the particles of the invention.

Extrusion techniques, along with optional milling or other mechanical attrition, may also be used to make Applicants' particles.

Microspheres are preferred particles.

II. Comestible Units

Comestible units made using the subject particles can be any of a variety of oral products. Among those contemplated are tablets, capsules, candies, liquid suspensions, gels and the like.

Generally, coated or uncoated particles made using the invention will be combined with other ingredients and used in such products.

If coatings are used, optimal disintegration properties are attained using coatings containing polymers or combinations of polymers that solubilize or hydrate quickly to facilitate hydration of the core. Water soluble cellulosics are operable.

Tableting can be carried out on a Killian tablet press or other suitable devices.

Capsules are generally gelatinous or made of similar substances. Added excipients are generally not needed. However, the capsules may be coated for tastemasking or other purposes.

Capsules may be made using conventional capsule-making machines.

DRAWINGS

FIG. 1 is a plot showing average percent of ibuprofen (IBP) dissolved in water vs. time, in minutes, for six samples of microspheres containing the drug/disintegrant/spheronization aid combination of Example 1. An assay value of 67.3% was used in making the calculations.

FIGS. 2 and 3 are photomicrographs of microspheres hydrated in pH 6.0 buffer.

FIG. 2 shows conventional, disintegrant-free spheres. The particles' maintaining spherical shapes means that dissolution is hampered.

FIG. 3 shows spheres made in accordance with Example 1. The clearly evident disintegration of the spheres enhances dissolution.

EXAMPLES

Example 1

Microspheres

Disintegratable microspheres were made from a composition containing 68% Ibuprofen, 20% Kollidon CL-M, 8% Compritol 888ATO and 4% Gelucire 50/13.

The procedure was:

Milled Gelucire was placed in a container with the other three ingredients and premixed in the bag. Part of the premix was put in a Cuisinart and mixed further; premix was added in increments until the first bag was empty. The final blend was hand-mixed.

The mix was poured into a thermoprocessor fitted with a V-groove insert, with the spin speed set at 5 Hz. Increasing the temperature to 40° C., the spin was increased to 60 Hz, and the duty cycle set to 14% to 15%.

When mix began to leave the head, incremental additions of mix were placed in the head, until all of the mix had been processed.

The microspheres were sieved to obtain those of about 150 to about 200 micron size. They were free-flowing, exhibiting little static charge.

Dissolution tests were run and the plot shown in FIG. 1 was prepared.

Example 2

Using the procedure described in Example 1, microspheres were made from a composition containing: 68% Ibuprofen, 16% Myvaplex 600P, 10% Crospovidone CL-M and 6% Gelucire 50/13. The microspheres have similar properties to those of Example 1.

Reasonable variations, such as those which would occur to a skilled artisan, may be made herein without departing from the scope of the invention.

We claim:

1. Disintegratable microspheres giving 100% aqueous dissolution in less than 30 minutes made from a composition comprising:

(a) about 50% to about 90% of at least one bio-affecting agent;

(b) about 2% to about 40% of at least one disintegrant; and (c) about 5% to about 15% by weight of at least one spheronization aid.

2. The microspheres of claim 1 wherein (c) is glyceryl behenate.

3. The microspheres of claim 2 wherein the composition also contains a polyethylene glycol glyceryl ester.

4. The microspheres of claim 3 wherein (a) contains at least one agent selected from the group consisting of: aspirin, ibuprofen, flurbiproten, nimesulide, and NMDA receptor antagonists.

5. The microspheres of claim 4 wherein (b) is cross-linked polyvinylpyrrolidone.

6. The microspheres of claim 5 wherein (a) contains ibuprofen.

7. A process for preparing a comestible unit which is 100% dissolved in water in less than 30 minutes comprising the steps of:

(1) making thermoformed particles, under heat processing conditions, from a composition comprising:
   (a) about 50% to about 90% of at least one bio-affecting agent;
   (b) about 2% to about 40% of at least one disintegrant; and
   (c) about 5% to about 15% of at least one spheronization (2) optionally grinding to yield microspheres, and (3) recovering the microspheres as solid disintegratable particles.

8. The process of claim 7 comprising the further step of:

(4) coating the microspheres of step (2) with at least one taste-masking coating.

9. The process of claim 8 comprising the further step of:

(5) preparing a comestible unit containing the coated microspheres of claim 8.

10. A comestible unit containing the microspheres of claim 1.

11. A comestible unit containing the microspheres of claim 1 coated with a taste-masking coating.

12. A method of preparing a disintegrating particle comprising the steps of:

(1) combining:
   (a) about 50 to about 90% of at least one bio affecting agent,
   (b) about 2 to about 40% of at least one disintegrant, and
   (c) about 5 to about 15% of at least one pheronization aid, (2) thermoprocessing the combination, and (3) recovering the thermoprocessed combination.

13. The method of claim 12 further comprising (4) milling or grinding the product of steps (3) to produce particles having generally round slopes.

14. The method of claim 13 wherein the particles produced are of about 150 to about 200 microns in diameter.

* * * * *